(12) United States Patent
Olmo et al.

(10) Patent No.: US 7,980,923 B2
(45) Date of Patent: Jul. 19, 2011

(54) POWDER BLAST TOOL, POWDER RESERVOIR, INSERT FOR POWDER RESERVOIR AND METHOD OF DENTAL TREATMENT

(75) Inventors: Olivier Olmo, Morges (CH); Marcel Donnet, Saint Jean de Gonville (FR)

(73) Assignee: Ferton Holding S.A. (CH)

( * ) Notice: Subject to any disclaimer, the term of this patent is extended or adjusted under 35 U.S.C. 154(b) by 302 days.

(21) Appl. No.: 12/047,869

(22) Filed: Mar. 13, 2008

(65) Prior Publication Data

US 2008/0233540 A1 Sep. 25, 2008

(30) Foreign Application Priority Data

Mar. 19, 2007 (EP) .................................. 07005599

(51) Int. Cl.
*B24C 9/00* (2006.01)
(52) U.S. Cl. ........................... 451/99; 451/100; 433/215
(58) Field of Classification Search .................... 451/99, 451/100; 433/215
See application file for complete search history.

(56) References Cited

U.S. PATENT DOCUMENTS

| 2,759,266 | A | * | 8/1956 | Cassani | 433/88 |
|---|---|---|---|---|---|
| 3,626,841 | A | * | 12/1971 | Schachter | 451/90 |
| 3,631,631 | A | * | 1/1972 | Greenstein | 451/90 |
| 3,924,335 | A | * | 12/1975 | Balamuth et al. | 433/119 |
| 4,494,932 | A | * | 1/1985 | Rzewinski | 433/88 |
| 4,648,840 | A | * | 3/1987 | Conger, Sr. | 433/125 |
| 4,770,632 | A | * | 9/1988 | Ryder et al. | 433/28 |
| 5,312,251 | A | * | 5/1994 | Jackson | 433/88 |
| 5,643,052 | A | * | 7/1997 | Delattre et al. | 451/21 |
| 5,927,977 | A | * | 7/1999 | Sale et al. | 433/86 |
| 6,030,212 | A | * | 2/2000 | Schuman et al. | 433/80 |
| 6,106,288 | A | * | 8/2000 | Brassil et al. | 433/88 |
| 6,293,793 | B1 | * | 9/2001 | Schuman et al. | 433/86 |
| 2002/0137005 | A1 | * | 9/2002 | Cevey et al. | 433/88 |
| 2003/0077552 | A1 | * | 4/2003 | Decosterd et al. | 433/84 |

FOREIGN PATENT DOCUMENTS

| EP | 1356782 A1 | * | 10/2003 |
|---|---|---|---|
| WO | WO 99/20197 | | 4/1999 |
| WO | WO 00/10772 | | 3/2000 |

* cited by examiner

*Primary Examiner* — Maurina Rachuba
(74) *Attorney, Agent, or Firm* — Ostrolenk Faber LLP (57) ABSTRACT

A powder blast tool for mixing a powder with a pressurised gas, having at least one powder reservoir, with supply lines for the pressurised gas, and a discharge line, which is connected to a discharge nozzle, at which a powder-gas mixture and optionally pressurised water are discharged, wherein the powder blast tool can preferably be connected to plural powder reservoirs simultaneously and exchangeably, wherein at least one receiving region with at least one mixture terminal and at least one gas terminal is disposed on the powder blast tool and wherein the powder reservoir has a coupling region for exchangeable connection of the powder reservoir to the powder blast tool. Also disclosed are a suitable powder reservoir and an insert for such powder reservoirs and a corresponding method of dental treatment.

15 Claims, 8 Drawing Sheets

POWDER BLAST TOOL, POWDER RESERVOIR, INSERT FOR POWDER RESERVOIR AND METHOD OF DENTAL TREATMENT

BACKGROUND

1. Technical Field

The present invention relates to a powder blast tool for mixing a powder with a pressurised gas, a powder reservoir suitable for this purpose, an insert suitable for this powder reservoir, a method of dental treatment, and a preferred use of the powder blast tool or of the method according to the invention.

2. Background Art

Powder blast tools or dental abrasive blast tools, in which a dental powder stored in a reservoir is supplied together with a gaseous carrier medium at a nozzle arrangement of a handset connected via a discharge line, in general being mixed with pressurised water, are known for example from EP 1 243 226 A2. Therein, a preferably exchangeable powder reservoir is so fixed to a powder blast tool that a quantity of powder stored in the powder reservoir is continuously transferred into a mixing chamber, the powder is mixed with the air stream passing through the mixing chamber and is supplied as a powder-air mixture to a handset and a discharge nozzle disposed thereon for the dental treatment. EP 0 097 288 B1 discloses a generic powder blast tool with a powder reservoir into which a pressurised gas is introduced, so that the powder therein is swirled and can be discharged via an outlet aperture as a powder-air mixture. The powder reservoir is in this case located in the powder blast tool and can be refilled with powder from the top each time.

EP 1 159 929 A2 discloses a powder blast tool with a powder reservoir and an additional exchangeable fluid reservoir, with which e.g. de-mineralised water can be supplied to the teeth as a flushing fluid. The powder blast tool in this case has the same configuration in principle as the tool according to EP 0 097 288 B1, i.e. the powder reservoir is permanently incorporated in the powder blast tool.

From EP 0 268 948 B1, a sealing device for a fluid reservoir is known. The sealing device is formed for screwing the fluid reservoir on to a mounting part, which is provided on the exterior of the powder blast tool. Thus the fluid reservoir can be mounted exchangeably on exterior of the powder blast tool.

From U.S. Pat. No. 1,664,369 it is known that the powder supplied in a powder reservoir is mixed in a metered manner with the gaseous carrier medium by means of a motor-driven conveyor screw. The conveyor screw is in this case disposed under an outlet aperture of the powder reservoir. The powder is mixed with the gas at the end of the conveyor screw.

From EP 0 119 735 B2, a powder reservoir is known in whose centre an elongate tube is incorporated, which has at the lower end two inlet apertures, through which on the one hand pressurised gas and on the other hand powder can enter, which is stored in the powder chamber and surrounds the elongate tube, the powder being carried along by the inflowing gas inside the elongate tube and upward, mixed with the gas, and discharged at the upper end of the powder reservoir via an outlet aperture.

The prior powder blast tools or the powder reservoirs and nozzle arrangements or inserts for powder reservoirs suitable for the same have various disadvantages. A powder reservoir permanently installed in the powder blast tool has the disadvantage that this can only be cleaned together with the tool itself and aseptic cleaning of the interior of the powder reservoir is barely possible. Furthermore, the powder reservoir always has to be refilled, i.e. the closures, seals etc. connected to the reservoir get dirty over time, so that the entire powder blast tool becomes unusable. Furthermore, the known powder blast tools have the disadvantage that these are suitable only for a certain type and grade of powder, i.e. if smaller or larger grain sizes are used for the powder or different powder compositions are used, the corresponding supply and nozzle arrangements are not suitable, so that either too much or too little powder is supplied together with the gas jet. If fine-grained powder is used with a grain size of less than 100 µm, in EP 0 119 735 B2 there is the risk that the air supply line may become blocked with powder.

Also, for a certain powder blast tool only very particular powder reservoirs can be used, which are matched exactly to the conveying or nozzle arrangement of the powder blast tool. Also the known conveying quantity of powder-gas mixture can only be modified by a change in pressure of the gas being supplied or a change in the supply of powder, the powder supply generally being dependent on the speed of the gas, i.e. the gas pressure and the corresponding nozzle arrangement.

SUMMARY

The object of the present invention is to improve the known powder blast tools or corresponding powder reservoirs and associated inserts and nozzle arrangements in such a manner that various types of powder and grades or mixtures can be used consecutively or even simultaneously with one and the same powder blast tool. Furthermore, the object of the present invention is to be able to use and adjust different powder types independently of one another with one and the same powder blast tool, i.e. various types of powder can be used and adjustments can be made accordingly.

A further object of the invention is to indicate a powder blast tool which is particularly user-friendly and permits rapid exchange of the different powder types and grades, without the powder reservoir having to be elaborately cleaned and disinfected. Furthermore, it is an object of the invention to indicate powder reservoirs which may be set for different powder types, in which the powder reservoir may be adjusted or changed simply and in a user-friendly manner to the corresponding powder, as well as the inserts and nozzles suitable for the same. Finally, it is an object of the present invention to be able to use plural powder types simultaneously, without the treating surgeon having to change the handset or the powder reservoir or to make different settings on the control panel.

The objects of the present invention are achieved by the embodiments disclosed and claimed herein.

The powder blast tool of the present invention has at least one powder reservoir with supply lines, which supply the pressurised gas to the powder supply for mixing, and a discharge line, which is connected to a discharge nozzle, at which a powder-gas mixture and optionally water are discharged under pressure. The discharge nozzle is in this case advantageously fixed to a handset, with which the treating surgeon can direct the powder-gas-water mixture in a controlled manner on to the area being treated. The powder blast tool of the present invention has at least one receiving region with at least one mixture terminal and at least one gas terminal, so that the powder reservoir is connectable to the powder blast tool in an exchangeable manner, the powder reservoir having a preferably standardised coupling region.

Advantageously, the powder blast tool has two receiving regions each with a mixture terminal and a respective gas terminal, to which different powder reservoirs may be connected to one coupling region. The coupling region of the powder reservoirs is in this case matched to the receiving region of the powder blast tool and is advantageously standardised. Thus different powder reservoirs can be connected to each of the receiving regions of the powder blast tool, since each receiving region has a corresponding gas terminal for supplying the gas to the powder and a corresponding mixture terminal for discharging the powder-gas mixture developed in the powder reservoir.

To this end, the coupling region of the powder reservoir has at least one gas inlet and at least one mixture outlet, which are connectable in a sealing-tight manner to the gas terminal and mixture terminal respectively of the powder blast tool. The coupling region of each powder reservoir thus has at least one gas coupling and one mixture coupling, so that the pressurised gas made available from the powder blast tool can penetrate into the powder reservoirs, can mix there with the powder and can be supplied as a powder-gas mixture via the mixture coupling back to the powder blast tool. From there, the powder-gas mixture can be supplied via the discharge line or a suitable hose to a handset, where it is discharged at the discharge nozzle fixed thereon or formed therein, preferably together with a water jet annularly surrounding the powder-gas mixture.

The coupling region of the powder reservoir according to a preferred embodiment of the invention has grooves or seats, which engage in the tongues or spigots of the receiving regions of the powder blast tool upon connecting of the powder reservoir to the powder blast tool. Thus a guide and fixing of the powder reservoir on the powder blast tool is achieved. At the same time, the grooves or seats and tongues or spigots are used for exact connecting of the gas inlet to the gas terminal and of the mixture outlet to the mixture terminal. The coupling region of the powder reservoir may further have coding means according to a further preferred embodiment of the present invention, which cooperate with electrical contacts of the receiving regions in such a manner that the powder blast tool receives data about the type of powder reservoir being used. These coding means are spigots or apertures disposed e.g. at certain positions on the coupling region, which engage in corresponding apertures or spigots on the receiving region of the powder blast tool and/or open or close corresponding electrical contacts on the powder blast tool, so that a contact pattern is formed in or on the receiving region of the powder blast tool which contains the corresponding data about the type of powder reservoir.

By the coupling region adapted to the receiving region(s) of the powder blast tool, different powder reservoirs, i.e. also different powder mixtures and mixture preparation methods are selected. According to the grain size, density, weight, composition and type of powder and according to the swirling method or nozzle arrangement in the powder reservoir, a wide variety of powder types and powder-gas mixtures can be used or produced for one and the same powder blast tool, without the receiving region of the powder blast tool or the coupling region of the powder reservoir having to be altered. According to the powder reservoir used, the coupling region is equipped with data transmitters by means of the coding means in order to indicate to the powder blast tool the powder-gas mixture which is available, although optionally these coding means can be dispensed with and the corresponding information be indicated in writing on the exterior of the powder reservoir so that the user then inputs this information in a control panel of the powder blast tool. Other data transmission means such as chip cards, magnetic strips or a RAM scanning device are also applicable.

If plural powder reservoirs are located on the powder blast tool in the corresponding receiving regions, these can be triggered selectively in that the pressurised gas enters one of the powder reservoirs via the gas terminal and into the gas inlet connected thereto in a sealing-tight manner, is mixed there in the powder reservoir with the powder and enters the discharge line as a powder-gas mixture via the mixture outlet and the mixture terminal connected thereto in a sealing-tight manner, the discharge line being connected to a discharge nozzle. The pressurised gas is then advantageously supplied via gas inlet and pressurised water can be supplied via a corresponding water inlet to the powder blast tool, the gas selectively being supplied to one of the exchangeably mounted powder reservoirs and the water being supplied direct or via an adjustable choke to the discharge line.

A powder reservoir according to the present invention for a powder blast tool has a powder receptacle, a gas inlet, a mixture outlet and a swirling chamber, in which pressurised gas swirls the powder and is discharged as a powder-gas mixture via an outlet aperture, the powder reservoir having a coupling region for the sealing-tight connection of the gas inlet disposed in the coupling region and the mixture outlet disposed in the coupling region to corresponding terminals of a powder blast tool.

Advantageously, the powder receptacle has different nozzle/line mounts and different inserts, so that depending on the powder being used different nozzle and swirling arrangements may be formed in the powder reservoir. Preferably, the powder receptacle is disposed exchangeably in the powder reservoir and is connected there in a housing to the coupling region in a sealing-tight manner. The nozzle/line mounts are preferably detachably arranged and connected to the powder receptacle in the coupling region in such a manner that the pressurised gas can enter the powder receptacle and there swirl the powder. Advantageously the powder receptacle is formed as a disposable article and is sealed with a removable cover foil, which after insertion of the powder receptacle in the powder reservoir is removed, so that the powder receptacle is ready for operation. According to another preferred embodiment of the invention, the entire powder reservoir is formed as a disposable article and can be disposed of after emptying of the powder, so that expensive cleaning and sterilising of the powder reservoir is superfluous.

According to a first preferred embodiment of the powder reservoir the powder receptacle has a nozzle mount holding a nozzle and an insert, which so receives the nozzle with an injection aperture that the pressurised gas is supplied via the gas inlet of the nozzle into the injection aperture, wherein the nozzle oriented substantially vertically upward in the injection aperture of the insert allows the gas to flow into a cylindrically or conically tapering mixing chamber of the insert, so that powder, which is in the powder receptacle around the insert and between the nozzle and the wall of the mixing chamber lies against the injection aperture, is carried along vertically upward by the gas, is mixed with the gas in the mixing chamber and is swirled in the swirling chamber. The swirling of the powder is effected partly already in the mixing chamber, but substantially in the swirling chamber located at the mixing chamber and above the insert, where the outlet aperture for discharge of the powder-gas mixture is also located.

According to a second preferred embodiment of the powder reservoir according to the invention, the powder receptacle has a line mount holding a gas line, so that the pressurised gas flows into the gas line via the gas inlet and is passed from this through the powder supply or past the powder supply into the upper region of the powder receptacle and is thus supplied to a nozzle disposed at the end of the gas line, in such a manner that the gas discharged from the nozzle swirls the powder in the swirling chamber, the nozzle being located above the powder level of the powder located in the powder receptacle and being oriented in the direction of the powder in order to swirl the same accordingly.

The powder receptacle is advantageously disposed in a housing and closed with a lid, which is located on the side of the powder reservoir opposite the coupling region. Preferably, the powder receptacle is disposed in a vertically standing, cylindrical housing and is exchangeable there, in particular as a disposable article. The different nozzle/line mounts are located on the lower and the lid on the upper end of the housing, the lid and/or the powder receptacle being fixable in the housing in a sealing-tight manner by means of a sealing part.

The different nozzle/line mounts are preferably fixed exchangeably by means of a preferably removable sealing cap applicable in a sealing-tight manner to a base part of the housing in the coupling region. The coupling region of the powder reservoir preferably has coding means in the form of spigots and/or apertures, which contain data about the type of powder reservoir. The outlet aperture for discharging the powder-gas mixture is preferably located on the upper end of the housing in the region of the lid, and the lid has guide formations which deflect the powder-gas mixture. By exchanging the lid and by the use of a different lid with different guide formations, which may deflect the powder-gas mixture into different directions inside the swirling chamber relative to the outlet aperture, the powder-gas jet can be modified more or less in terms of the outlet aperture. Thus a simple regulating method is achieved without the powder blast tool or the powder reservoir having to be modified for this purpose.

Preferably, the housing of the powder reservoir is transparent at least in part in order that the treating surgeon is informed of the fill level of the powder receptacle.

According to a further preferred embodiment of the invention, the coupling region has locking means which fix the powder reservoir with corresponding means on the powder blast tool, so that the user can safely assume that the gas and mixture couplings are securely connected together in a sealing-tight manner.

An insert according to the invention for a powder reservoir according to the present invention has segments which form different sizes of regulating aperture, which can be selectively disposed in front of the outlet aperture in order thus to regulate the ejection of powder-gas mixture. The segments preferably form sections of a circle and are fixed by means of support webs to the cylindrically or conically tapering mixing chamber. The insert has substantially the form of an elongate, hollow pin, on whose lower end the injection aperture is disposed, into which the nozzle projects for injection of the gas, whilst at the other end the circular segments are arranged spaced apart from the mixing chamber by means of support webs, in such a manner that they abut the upper outer edge of the powder receptacle and the cover the outlet aperture in the rotated state or expose the same in the region of the regulating apertures. Between the circular segments, regulating apertures are provided, which have different sizes so that upon rotation of the insert in the powder receptacle different sizes of regulating apertures can be placed in front of the outlet aperture, so that thus regulation of the powder-gas mixture can be set. Advantageously, the support webs engage in rotary limits of the powder receptacle in order to be able to dispose a specifiable regulating aperture exactly in front of the corresponding outlet aperture.

The injection aperture at the lower end of the pin-like insert differs from the injection aperture of the pin-like mixing chamber of U.S. Pat. No. 4,487,582, in which the nozzle projects into the pin-like insert and an annular gap is formed between the nozzle and the injection aperture which—depending on the grain size of the powder used—must be of a different dimension. Powder cannot penetrate through the annular gap into the mixing chamber, but is only carried and swirled by the pressurised gas as this is injected. By this arrangement of the nozzle according to the invention, blocking of the nozzle by trickling back of the powder is avoided, since the annular gap between the nozzle and injection aperture of the pin-shaped insert prevents the powder from moving back when the gas is switched off.

The cylindrically or conically tapering mixing chamber of the insert is adaptable to the powder being used in its length, diameter, diameter change in the flow direction and its distance from the nozzle, so that by exchanging the insert the powder receptacle can be adapted in its swirling effect and in its ability to swirl certain powders reliably and evenly.

The method according to the present invention for dental treatment uses a powder blast tool, in which a pressurised gas is mixed with a powder, the gas being supplied via supply lines to a powder reservoir and there mixed with the powder, the gas-powder mixture being supplied via a discharge line to a discharge nozzle, which is preferably located on a handset. The powder reservoir which has a coupling region to a gas inlet and to a mixture outlet is connected to the powder blast tool, which has at least one receiving region with at least one mixture terminal and at least one gas terminal, in which the gas inlet is connected in a sealing-tight manner to the gas terminal and the mixture outlet is connected in a sealing-tight manner to the mixture terminal.

According to a preferred embodiment of the method according to the invention, two different powder reservoirs are connected to the powder blast tool, wherein a first powder reservoir has a first powder with a first suitable nozzle arrangement and a second powder reservoir has a second powder with a second suitable nozzle arrangement, both powder reservoirs having similar coupling regions for connecting to the powder blast tool and the pressurised gas selectively being supplied to one or other of the powder reservoirs.

A preferred use of the powder blast tool according to the invention or of the method according to the invention is the use in abrasive cleaning of teeth and simultaneously cleaning of the gingival pockets. To this end, two different types of powder are necessary with two different powder-gas mixture compositions at different pressures, since for abrasive cleaning of teeth e.g. aluminium oxide or dolomite can be used if with the powder less gentle cutting operations or the removal of particularly stubborn calculus is to be carried out. In the cleaning of the gingival pockets, however, a finer-grained, gentler powder is needed, which simultaneously should develop an antibacterial effect. Here for example, sodium carbonate is suitable, with which antibacterial and decay-inhibiting additives are mixed. Whilst for fine-grained powders nozzle arrangements are suitable which act on the powder direct with the gas, it has been found that coarser-grained powders can be better swirled with a nozzle arrangement and are disposed in an injection aperture of an insert, so that the powder is carried along with and swirled by the gas flowing past the injection aperture.

As a preferred gas, air is used, and this is preferably supplied to the powder blast tool via a compressed air terminal, but it is also conceivable that the powder blast tool itself contains a compressor and produces the compressed air itself. The powder reservoirs are furthermore closed in a sealing-tight manner so that escape of the powder, as well as penetration of dirt and damp are prevented. To this end, preferably located between the powder receptacle and the coupling region and between the nozzle/line mount and the sealing cap or between the latter and the base part corresponding seals, preferably composed of rubber, are provided. Due to the exchangeable nature of the powder reservoirs, different types of powder can be made available and different powder-gas or powder-air mixtures can be prepared and used.

Other features and advantages will become apparent from the following description of embodiments, which refers to the accompanying drawings.

BRIEF DESCRIPTION OF THE DRAWINGS

A few preferred embodiments of the present invention are explained more fully by means of the attached drawings, which show.

DETAILED DESCRIPTION

Figure 1:
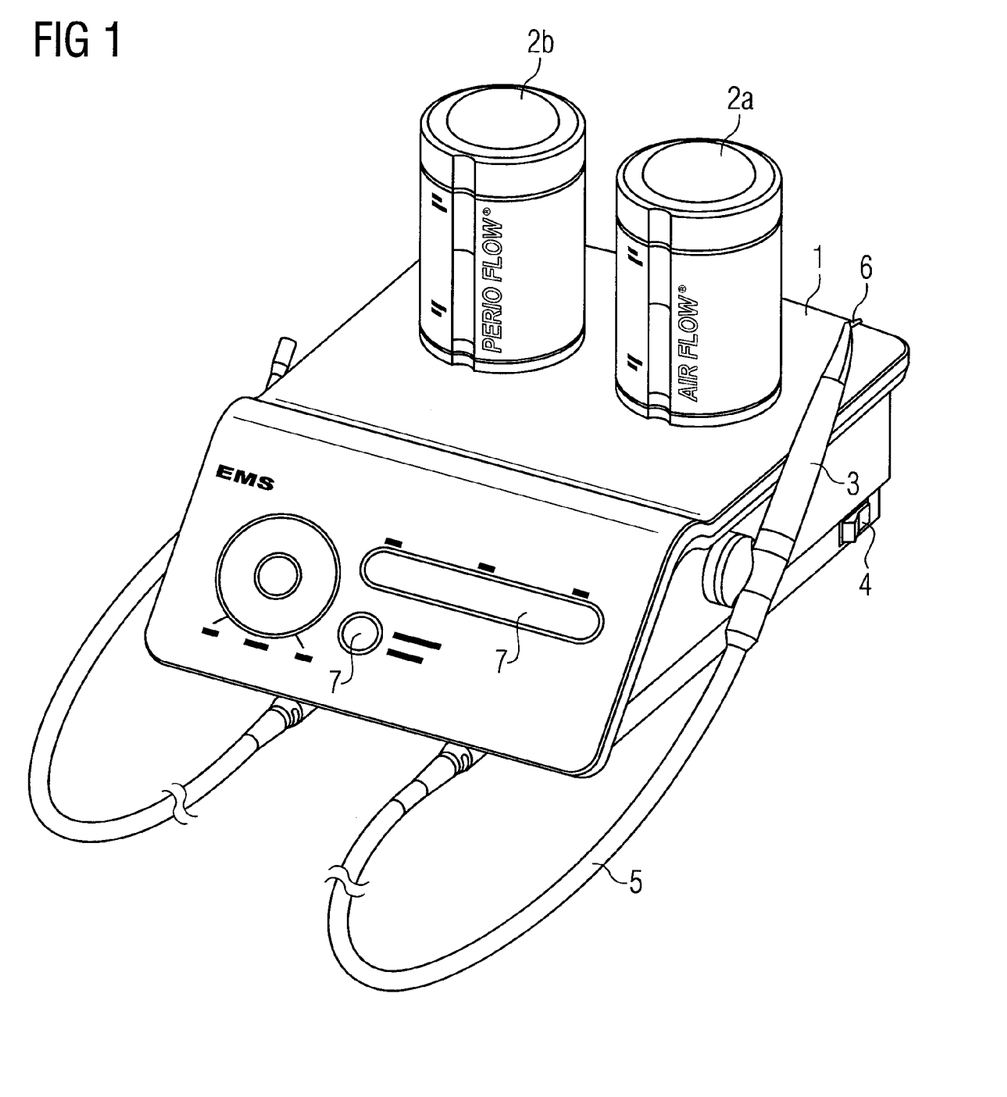
FIG. 1 a schematic, three-dimensional view of a powder blast tool according to the invention with two mounted powder reservoirs according to the invention.

FIG. 1 shows the three-dimensional front view of a powder blast tool 1 according to the invention with a first powder reservoir 2a and a second powder reservoir 2b, which are mounted on the upper side of the powder blast tool 1. The powder blast tool 1 has a control panel 7 for setting the strength of the powder-gas mixture, the strength of the water jet and for selecting the powder reservoir 2a, 2b to be used. Fixed to the powder blast tool 1 is a discharge line 5, which opens into a handset 3, to which a discharge nozzle 6 is fixed, at which the powder-gas mixture and the water are discharged. A switch 4 is used for switching the powder blast tool 1 on and off.

Figure 2:
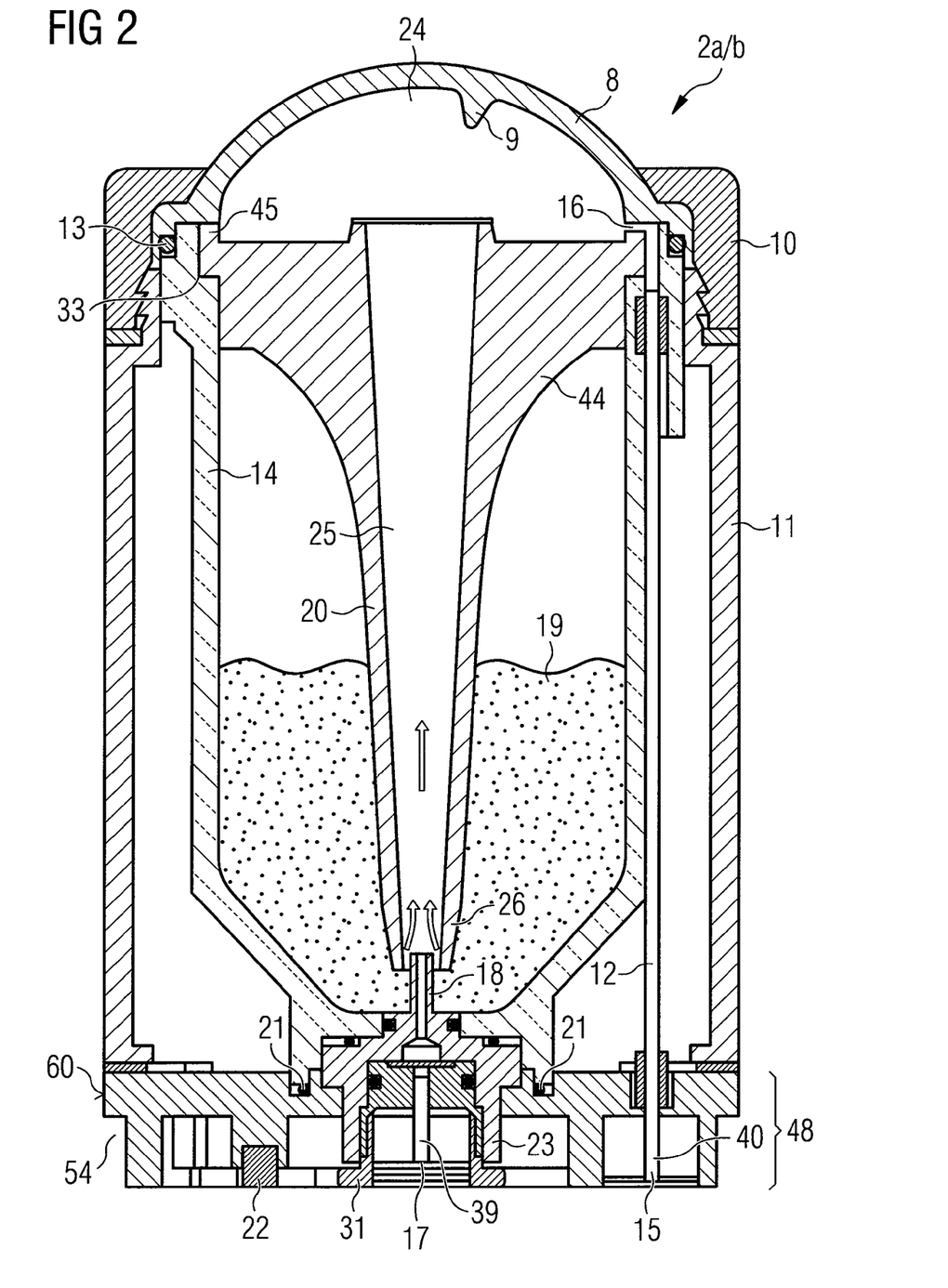
FIG. 2 a cross-section through a first preferred embodiment of a powder reservoir according to the invention.

FIG. 2 shows a first preferred embodiment of the powder reservoir 2 with a housing 11, in which a powder receptacle 14 is inserted and fixed in a sealed manner. The powder receptacle 14 is positioned substantially upright in a preferably cylindrically formed housing 11, and is fixed in a sealing-tight manner by means of a sealing part 10 to the upper end of the housing 11 optionally together with a lid 8. At the lower part of the housing 11 is a base part 60, to which the powder receptacle 14 is fixed in a sealing-tight manner.

In the powder receptacle 14 is an insert 20, which forms a cylindrical or substantially conically tapering elongate mixing chamber 25 and has in the upper region of the housing 11 associated with the lid 8 support webs 44 which support segments 45. The insert 20 has at the lower end associated with the base part 60 an injection aperture 26, into which a nozzle 18 opens, which by means of a nozzle mount 23 is fixed to the housing 11 or to the base part 60 in a sealing-tight manner. For exchanging the nozzle 18, the nozzle mount 23 is preferably mounted exchangeably by means of a sealing cap 31. The sealing cap 31 is fixed relative to the nozzle mount 23 to the base part 60 in a sealing-tight manner, the nozzle 18 being connected to a gas connecting piece 39, which forms a gas inlet 17 and is used as a coupling for coupling to a gas terminal of the powder blast tool 1. In order that the gas can reliably enter the nozzle 18 via the gas connecting piece 39, the sealing cap 31 is also sealed relative to the nozzle mount 23 by means of a membrane seal 27 (cf. FIG. 3).

The base part 60 defines in the embodiment shown here also the coupling region 48 of the powder reservoir 2, which in addition to the nozzle mount 23 with sealing cap 31 and gas connecting piece 39 also has a mixture outlet 15 with a mixture connecting piece 40, which preferably opens continuously into a mixture line 12, which is connected at the upper end of the power receptacle 14 to an outlet aperture 16, so that the powder-gas mixture can be discharged at the mixture outlet 15 along the mixture line 12 via the outlet aperture 16. The mixture line 12 is likewise sealed with respect to the base part 60. Finally, the coupling region 48 preferably has spigots 22, which engage with electrical contacts 37 (cf. FIG. 6) in such a manner that the powder blast tool 1 receives data about the type of powder reservoir 2.

The powder receptacle 14 has a certain quantity of powder 19 stored, which fills the powder receptacle 14 around the insert 20 up to a certain fill level and is applied against the injection aperture 26 in the region of the nozzle 18. The powder 19 does not fill the mixing chamber 25 in the resting state due to the inherent properties of the powder, since this locks together in the annular gap between the wall of the injection aperture 26 of the insert 20 and the nozzle 18 and forms a limit layer there.

As soon as pressurised gas is discharged from the nozzle 18, a vacuum forms at the annular gap between the nozzle 18 and the chamber wall of the mixing chamber 25 and carries away the powder there in an upward direction (cf. arrows indicated), so that the gas mixes with the powder in the mixing chamber 25 and is swirled therein also in part, until it is discharged from the insert 20 upwards and into the swirling chamber 24. In the swirling chamber 24, the gas-powder mixture is swirled and partly discharged via the outlet aperture 16, and partly returned back to the powder receptacle 14.

The lid 8 preferably has guide formations 9, which regulate the swirling direction and the quantity of powder-gas mixture which reaches the outlet aperture 16.

The insert 20 can be inserted into various positions in the powder receptacle 14, which has rotation limits 33, into which the corresponding support webs 44 and/or segments 45 engage, so that special regulating apertures 43 (cf. FIG. 8) abut the outlet aperture 16 and there form a certain width of aperture for the powder-gas mixture.

Figure 9:
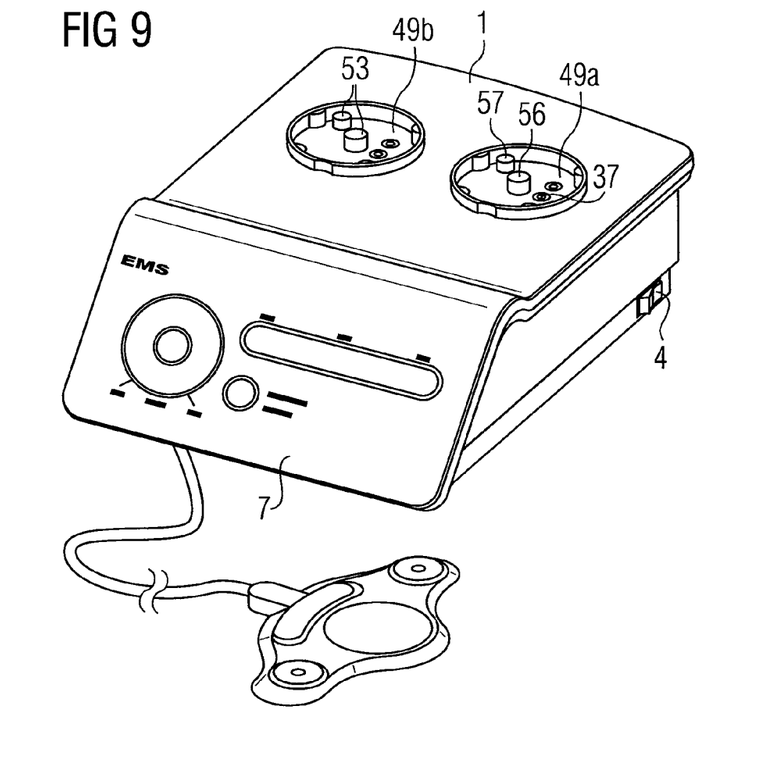
FIG. 9 a three-dimensional front view of a powder blast tool according to the invention without the powder reservoir mounted having two receiving regions and FIG. 10 a three-dimensional rear view of the powder blast tool according to the invention with two receiving regions but without a powder reservoir.
Figure 10:
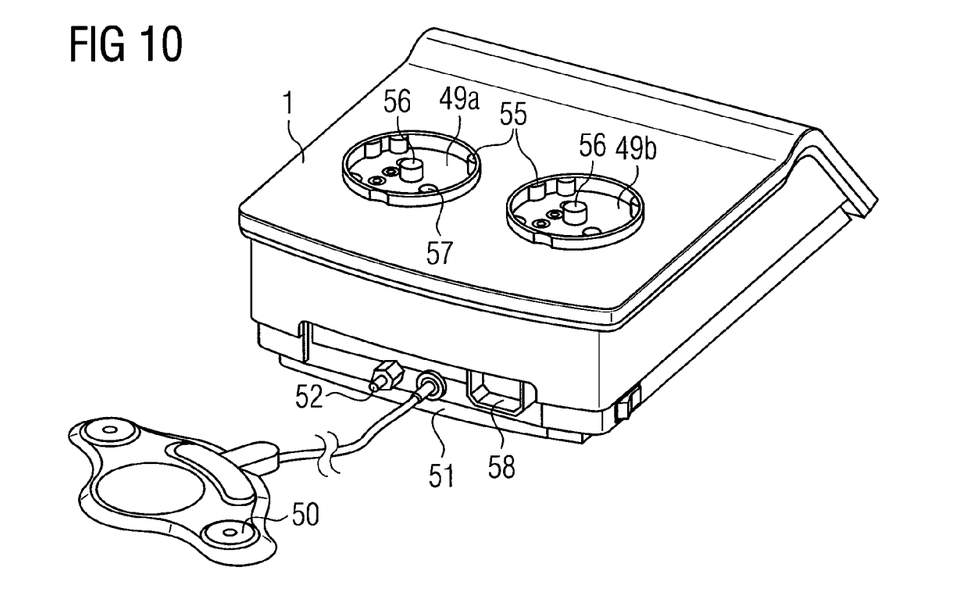

The base part 60 preferably has grooves 54, which engage in corresponding tongues 55 (cf. FIGS. 9/10). Thus exact positioning of the powder reservoir 2 on the powder blast tool 1 is ensured. Furthermore, the connections of powder receptacle 14 to base part 60 are sealed via reservoir seals 21, preferably O-rings.

Figure 3:
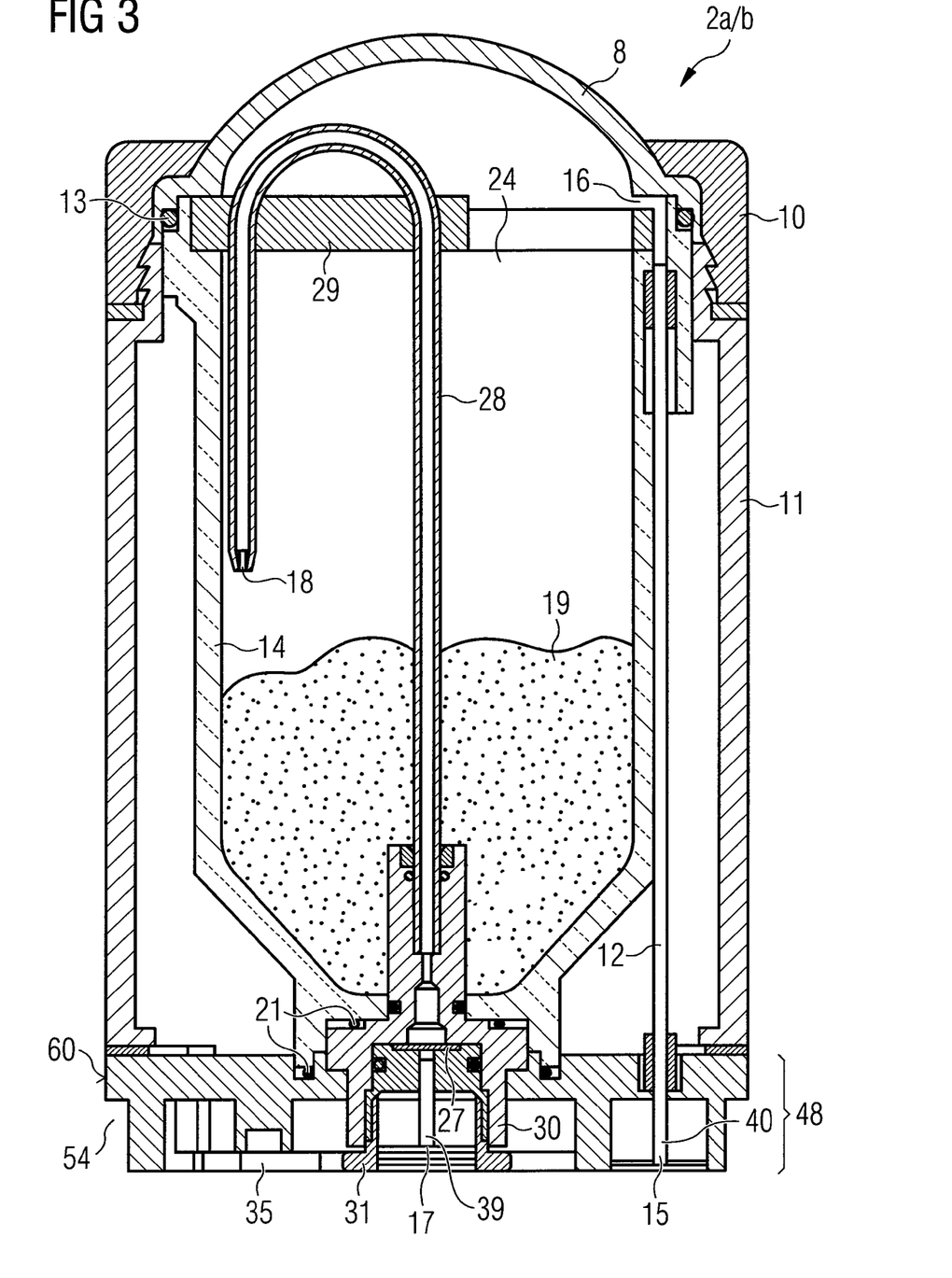
FIG. 3 a cross-section through a second preferred embodiment of a powder reservoir according to the invention.

FIG. 3 shows a second preferred embodiment of a powder reservoir 2 according to the present invention. The same parts are provided with the same reference numbers so that the description to FIG. 2 can be referred to. Instead of a nozzle mount 23, in this embodiment a line mount 30 is fixed in the base part 60 in a sealing-tight manner and carries a gas line 28, which extends inside the powder receptacle 14 upward to a connecting link 29, there describes a 180° loop and is oriented back down at the edge of the powder receptacle 14 in the direction of the powder, so that a nozzle 18 located at the end of the gas line 28 is directed at the powder 19. The line mount 30 is like the embodiment according to FIG. 2 preferably exchangeably fixed in a sealing-tight manner to the housing 11 by means of a sealing cap 31 and is sealed with respect to the powder receptacle 14 and the sealing cap 31 with corresponding housing seals 21. Instead of a spigot 22, in the coupling region 48 is an aperture 35, which transmits to the powder blast tool 1 a different coding from the first embodiment according to FIG. 2. Thus the powder blast tool 1 receives the information that a powder reservoir 2 with a gas line 28 has been mounted, but not with an insert 20.

The gas, preferably compressed air, flowing in through the gas inlet 17 runs through the membrane seal 27 into the gas line 28 and is directed via the nozzle 18 on to the powder. The preferably fine-grained, finely mixed powder 19 is swirled in the swirling chamber 24, which is formed by the powder receptacle 14 and the upper region of the housing 11 below the lid 8. The swirled powder leaves the swirling chamber 24 via the outlet aperture 16 and is discharged by means of the mixture line 12 and the mixture connecting piece 40 at the mixture outlet 15.

Figure 4:
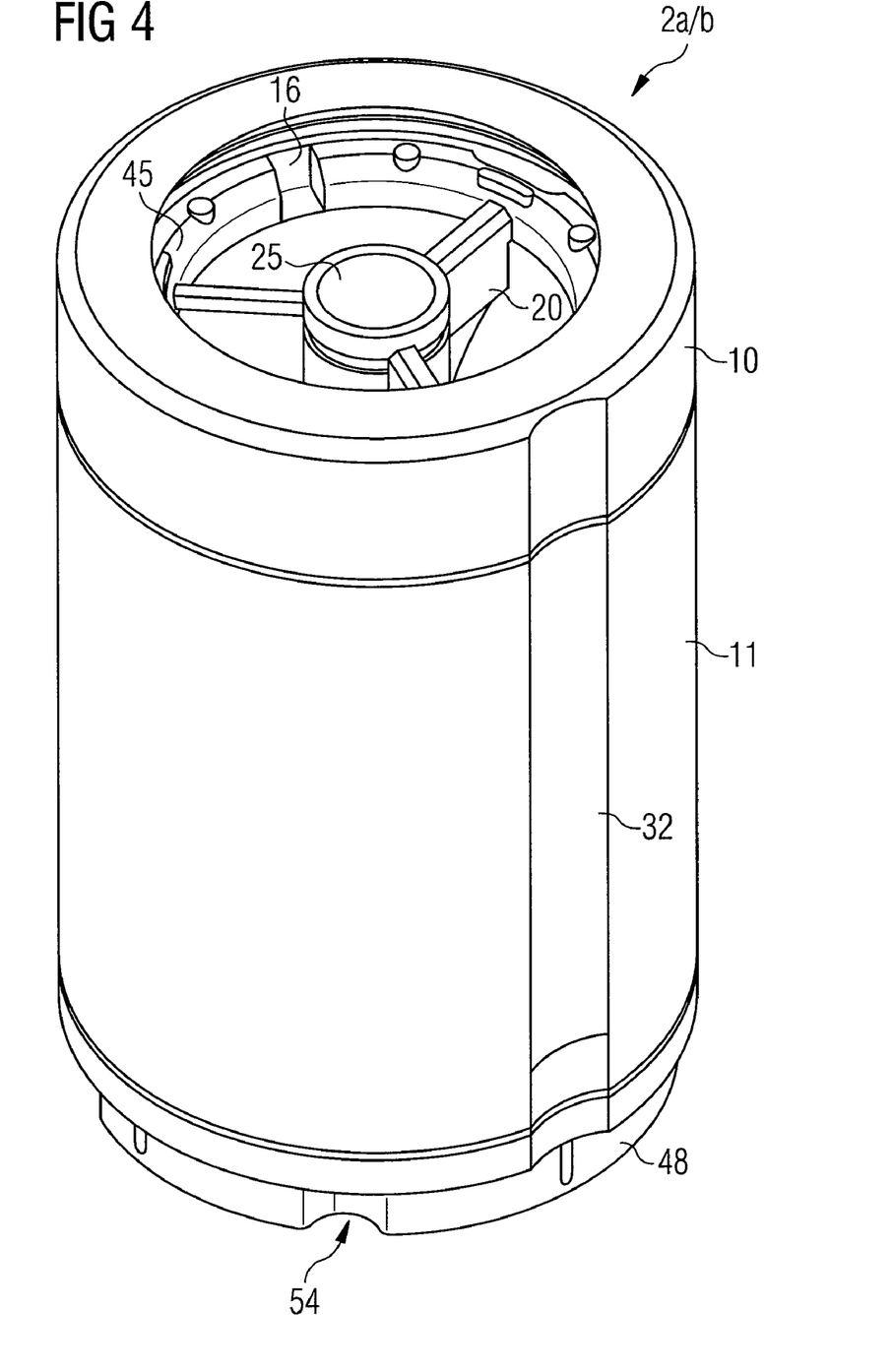
FIG. 4 a three-dimensional view of the first preferred embodiment of a powder reservoir according to the invention according to FIG. 2.

FIG. 4 shows a three-dimensional view of the first preferred embodiment of the powder reservoir 2 with insert 20, the housing 11 having a transparent inspection window 32, by which the fill level of the powder supply can be scanned. Optionally, the housing 11 may also be formed completely of a transparent material, such as plastics or glass.

At the lower end at the coupling region 48 are grooves 54 for the non-rotatable mounting on the receiving region 49 of the powder blast tool 1. FIG. 4 shows the upper region of the housing 11 with sealing part 10, but with the lid 8 removed, whereby the segments 45 of the insert 20 can be seen which form the regulating apertures 43, behind which a single tubular outlet aperture 16 or selectively an annular outlet aperture 16 is located, which discharges powder via all available regulating apertures 43 and discharges the same at one side of the powder reservoir 2 via the mixture line 12.

Figure 5:
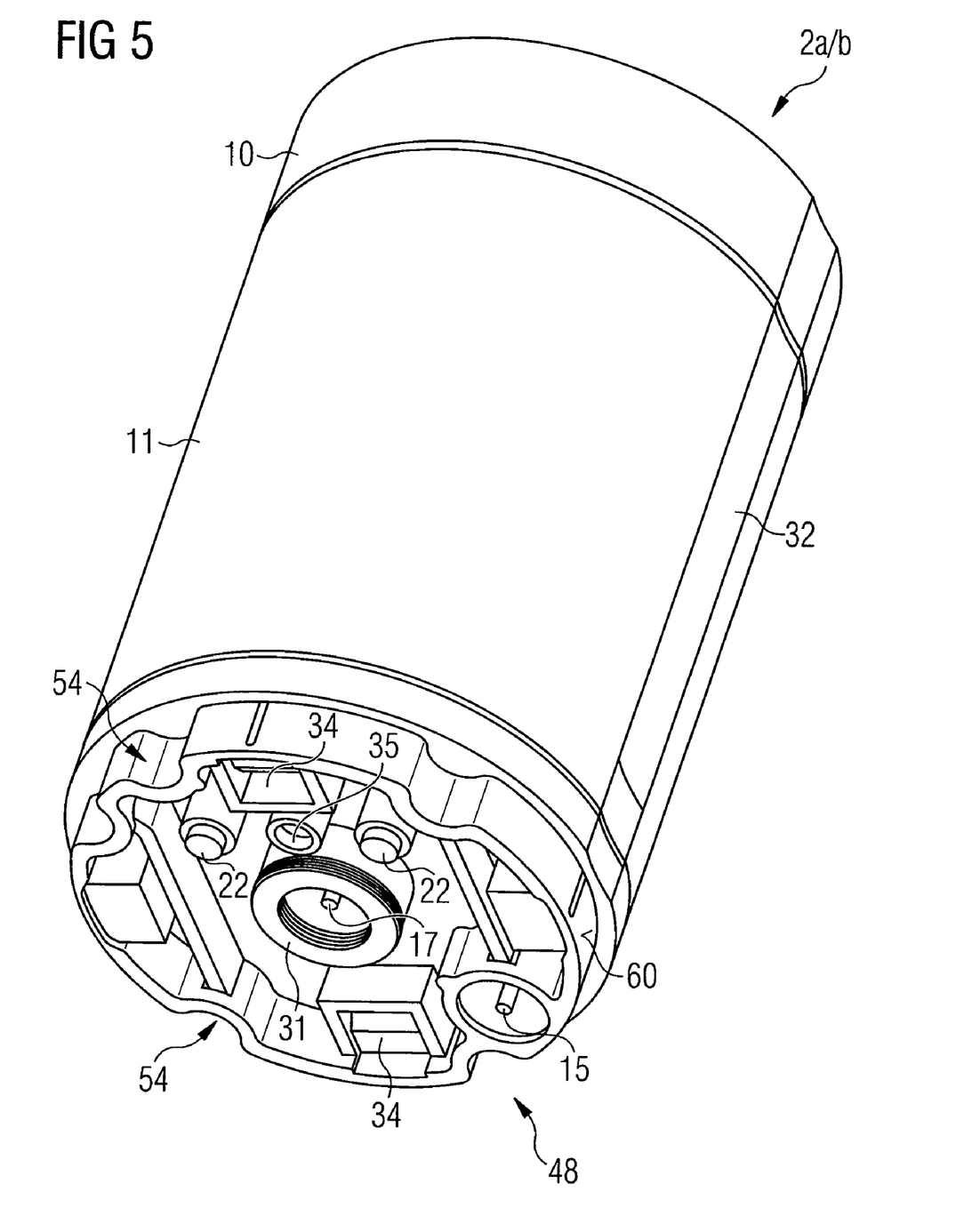
FIG. 5 a three-dimensional view obliquely from below of a powder reservoir according to the invention.

FIG. 5 shows a three-dimensional lower view of a powder reservoir 2 according to the invention with an upper sealing part 10 and inspection window 32. The lower region of the housing 11 forms the coupling region 48, which preferably consists of a base part 60, which runs round the circumference of the preferably cylindrical housing 11 in an annular manner with a slightly reduced diameter around the powder reservoir 2, segment-like grooves 54 being provided for mounting on the powder blast tool 1.

Spigots 22 or apertures 35 can be seen which are for coding of the powder reservoir 2. Furthermore, seats 34 can be provided into which corresponding spigots of the receiving region of the powder blast tool 1 engage in order to secure the powder reservoir 2 further.

The gas inlet 17 can be seen inside the sealing cap 31, which is preferably inserted helically and which fixes the nozzle mount 23 or the line mount 30.

Figure 6:
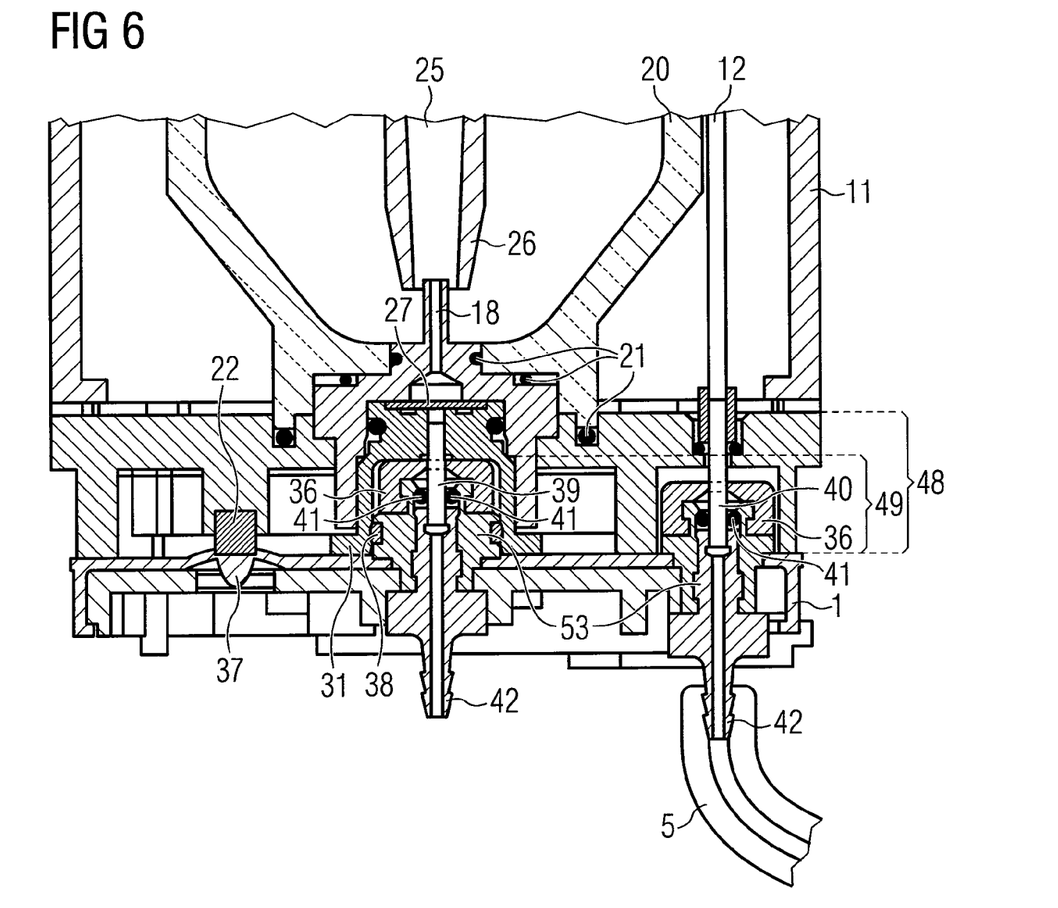
FIG. 6 a partial cross-section through the lower part of the powder reservoir according to the invention according to a first embodiment according to FIG. 2 with coupling region and a cross-section through the upper region of the powder blast tool with a receiving region.

FIG. 6 shows the cross-section through the lower region of the powder reservoir 2 according to a first preferred embodiment according to FIG. 2 and the cross-section through the upper region of the powder blast tool 1, i.e. through the receiving region 49, which mostly coincides with the coupling region 48 of the powder reservoir 2.

The powder blast tool 1 has plug-in projections 42, which can be connected to corresponding compressed air lines or mixture lines. Via a first plug-in projection 42, compressed air is supplied to the gas connecting piece 39, which feeds the gas via the membrane seal 27 to the nozzle 18. Upon insertion of the powder reservoir 2 into the receiving region 49 of the powder blast tool 1, the gas connecting piece 39 penetrates a perforated sealing cap 36, which preferably consists of rubber, providing a first sealing effect. Furthermore, below the sealing cap 36 a connecting seal 41 is located, preferably a rubber O-ring, which reliably seals the gas connecting piece 39 with respect to the sealing cap 36 and the surroundings.

In the same way, the mixture connecting piece 40 is also pushed through a perforated sealing cap 36 and is sealed there by means of a connecting seal 41 with respect to the surroundings. The mixture runs through the mixture line 12 and the mixture connecting piece 40 into the plug-in projection 42 and can there be received by the discharge line 5.

Furthermore, a spigot 22 can be seen which presses against an electrical contact 37 and thus forwards the information to the powder blast tool 1 as to which powder reservoir 2 is currently mounted on the powder blast tool 1 or on the selected receiving region 49.

Figure 7:
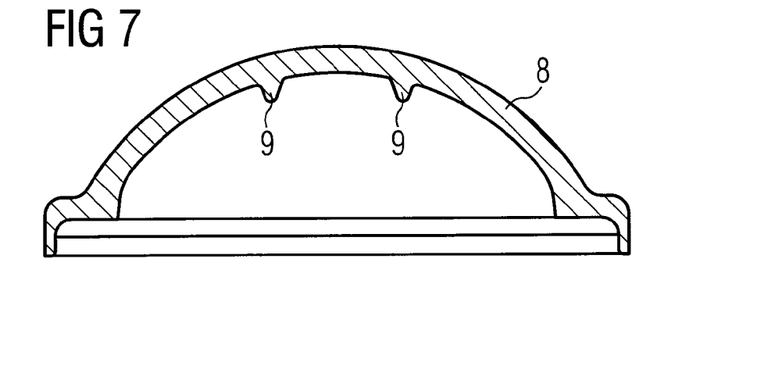
FIG. 7 a cross-section through a preferred embodiment of the lid of the powder reservoir according to the invention.

FIG. 7 shows a cross-section through a preferred lid 8 with guide formations 9. These can be disposed at different points in such a manner that the powder-gas mixture developed in the swirling chamber 24 is deflected more or less in the direction of the outlet aperture 16. Thus different lids 8 may be added to a powder blast tool 1 or a powder reservoir 2 so that the surgeon can quickly unscrew the sealing part 10 and exchange the lid 8 in order to achieve a different mixture quality.

Figure 8:
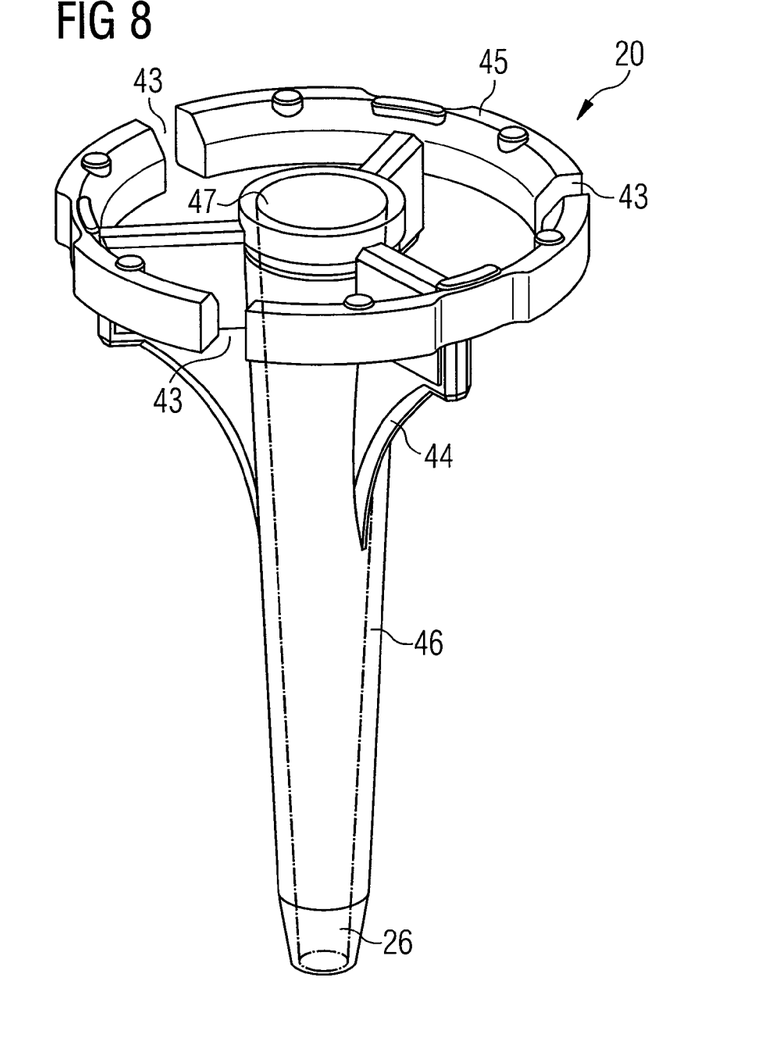
FIG. 8 a three-dimensional view of an insert for the first preferred embodiment of the powder reservoir according to the invention according to FIG. 2.

FIG. 8 shows a three-dimensional view of an insert 20 according to the invention with a riser 46 which is formed substantially slightly cylindrically or conically tapering and which forms an injection aperture 26 at the lower region, into which the nozzle 18 easily projects. At the upper side of the riser 46 remote from the injection aperture 26 are segments 45, which are disposed annularly around the upper outlet 47 of the riser 46 and are mounted by means of support webs 44 on the riser 46. By different lengths or extents of segments 45, different regulating apertures 43 are formed, which can then be placed opposite an outlet aperture 16 by rotation of the insert 20. By removing the insert 20, rotation and resetting, optionally with exchange of the lid 8 with different guide formations 9, a completely different powder-gas mixture composition can be achieved without having to exchange or alter the powder reservoir 2.

Optionally, on the upper region of the housing 11 however, an annular, slotted outlet aperture 16 can be provided so that the powder-gas mixture can be discharged through all the regulating apertures 43 to the outside, again different sizes of regulating apertures 43 being responsible for the quantity of powder-gas mixture. In this case, the mixture quality is possible by exchanging the insert 20 with different sizes of regulating apertures 43.

FIGS. 9 and 10 show the powder blast tool 1 according to the invention obliquely from the front and back respectively, wherein in the upper region of the housing two receiving regions 49 are indicated, a first receiving region 49a having a gas terminal 56 and a mixture terminal 57, i.e. terminals 53, to which corresponding coupling parts of the powder reservoir 2 can be connected. The receiving region 49a, 49b further preferably has contacts 37, which coincide with corresponding spigots 22 or apertures 35, in order to detect the coding means of the powder reservoir 2. The receiving region 49 further has tongues 55 which engage in corresponding grooves 54 for non-rotatable fixing of the powder reservoir.

If the powder reservoir is inserted into the receiving region 49, thus as is shown in FIG. 6, preferably a clamping ring 38 is used, which is disposed in the lower region of the gas terminal 56 for engagement in a groove-like recess on the sealing cap 31, in order thus to lock the powder reservoir 2 securely. Furthermore, the powder blast tool 1 according to the invention has an electrical terminal 58 and a foot switch 50, which is connectable to the lower region. At the rear region of the powder blast tool 1, preferably a water inlet 51 is provided and a gas inlet 52, such as for example a compressed air terminal.

By means of the foot switch 50, just as with the control panel 7, individual powder reservoirs 2 can be selected and the strength of the powder-gas mixture or the strength of the water jet can be set. The foot switch 50 is used in particular for comfortable operation of the powder blast tool 1 during the dental treatment. The lid 8 of the powder reservoir 2 may, like the housing 11, be formed transparent in order to permit easy checking of the fill level in the powder reservoir. Also, when the tool is running, faults can be easily recognised at a glance.

Although the present invention has been described in relation to particular embodiments thereof, many other variations and modifications and other uses will become apparent to those skilled in the art. Therefore, the present invention is not limited by the specific disclosure herein.

What is claimed is:

1. Powder reservoir for a powder blast tool, having a powder receptacle, a gas inlet, a mixture outlet and a swirling chamber, in which pressurised gas swirls powder and a powder-gas mixture may be discharged via an outlet aperture,
   characterised in that the powder reservoir has a coupling region for sealing-tight connection of the gas inlet disposed in the coupling region and of the mixture outlet disposed in the coupling region to corresponding terminals of a powder blast tool; and
   comprising means for receiving different nozzle/line mounts and different inserts, so that according to the powder being used different nozzle and swirling arrangements may be realised.

2. Powder reservoir according to claim 1, characterised in that the powder receptacle receives a nozzle mount holding a nozzle and an insert with an injection aperture in such a manner that the pressurised gas may be supplied via the gas inlet to the nozzle, which in the injection aperture of the insert, oriented substantially vertically upward, allows the gas to flow into a cylindrically or conically tapering mixing chamber of the insert, so that powder, which is located in the powder receptacle around the insert and is located between the nozzle and the wall of the mixing chamber against the injection aperture is carried vertically upward with the gas, is mixed with the gas in the mixing chamber and is swirled in the swirling chamber.

3. Powder reservoir according to claim 1, characterised in that the powder receptacle receives a line mount holding a gas line in such a manner that the pressurised gas may be supplied via the gas inlet to the nozzle disposed at the end of the gas line in such a manner that the gas discharged from the nozzle swirls the powder in the swirling chamber, the nozzle being directed above a powder level of a powder located in the powder receptacle at the powder.

4. Powder reservoir according to claim 1, characterised in that the powder receptacle is disposed in a housing and is closed with a lid, which is located on the side of the powder reservoir opposite the coupling region.

5. Powder reservoir for a powder blast tool, having a powder receptacle, a gas inlet, a mixture outlet and a swirling chamber, in which pressurised gas swirls powder and a powder-gas mixture may be discharged via an outlet aperture,
   characterised in that the powder reservoir has a coupling region for sealing-tight connection of the gas inlet disposed in the coupling region and of the mixture outlet disposed in the coupling region to corresponding terminals of a powder blast tool; and
   characterised in that the powder receptacle is disposed in an upright cylindrical housing in an exchangeable manner, the different nozzle/line mounts being located at the lower end and the lid at the upper end of the housing, and the lid and/or the powder receptacle are fixable by means of a sealing part in the housing in a sealing-tight manner.

6. Powder reservoir according to claim 1, characterised in that the powder receptacle is disposed in a housing, and the different nozzle/line mounts are fixed exchangeably to a base part of the housing by means of a removable sealing cap.

7. Powder reservoir according to claim 1,
   characterised in that the coupling region of the powder reservoir has coding means in the form of spigots and/or apertures, which contain data about the type of powder reservoir.

8. Powder reservoir according to claim 5, characterised in that the outlet aperture is disposed at the upper end of the housing and in the region of the lid, and the lid has guide formations which deflect the powder-gas mixture.

9. Powder reservoir according to claim 4, characterised in that the housing is transparent at least in part.

10. Powder reservoir according to claim 1, characterised in that the coupling region has locking means, which fix the powder reservoir with corresponding counter-means on the powder blast tool.

11. Powder reservoir according to claim 2, characterised in that the insert has segments, which form different sizes of regulating apertures, which can be disposed selectively in front of the outlet aperture in order thus to regulate the ejection of powder-gas mixture.

12. Powder reservoir according to claim 11, characterised in that the segments are segments of a circle and are fixed by means of support webs to the cylindrically or conically tapering mixing chamber.

13. Powder reservoir according to claim 12, characterised in that the support webs engage in rotation limits of the powder receptacle so that a specifiable regulating aperture is disposed selectively in front of the outlet aperture.

14. Powder reservoir according to claim 11, characterised in that the cylindrically or conically tapering mixing chamber is adaptable in its length, diameter, diameter change in the flow direction and in its distance from the nozzle to the powder respectively being used.

15. Powder reservoir according to claim 5,
   characterised in that the coupling region of the powder reservoir has coding means in the form of spigots and/or apertures, which contain data about the type of powder reservoir.

* * * * *